(12) United States Patent
Hakozaki et al.

(10) Patent No.: US 10,874,600 B2
(45) Date of Patent: *Dec. 29, 2020

(54) METHOD FOR DEGRADING BILIRUBIN IN SKIN

(71) Applicant: The Procter & Gamble Company, Cincinnati, OH (US)

(72) Inventors: Tomohiro Hakozaki, Cincinnati, OH (US); Bin Fang Deyer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/010,944

(22) Filed: Jun. 18, 2018

(65) Prior Publication Data

US 2019/0380945 A1 Dec. 19, 2019

(51) Int. Cl.
*A61K 8/67* (2006.01)
*A61Q 19/00* (2006.01)

(52) U.S. Cl.
CPC .............. *A61K 8/675* (2013.01); *A61Q 19/00* (2013.01); *A61K 2800/48* (2013.01)

(58) Field of Classification Search
CPC ...................................................... A61K 8/675
See application file for complete search history.

(56) References Cited

U.S. PATENT DOCUMENTS

| 6,238,678 B1 | 5/2001 | Oblong et al. |
| H002013 H | 2/2002 | Boyd et al. |
| 7,332,152 B2 | 2/2008 | Sanzgiri |
| 2004/0081672 A1 | 4/2004 | Gupta |
| 2004/0092482 A1 | 5/2004 | Gupta |
| 2006/0147508 A1 | 7/2006 | Gupta |
| 2010/0105638 A1* | 4/2010 | Den-Braven ............ A61K 8/67 514/99 |
| 2012/0189684 A1 | 7/2012 | Buckley |
| 2017/0196795 A1 | 7/2017 | Hakozaki |

FOREIGN PATENT DOCUMENTS

| WO | WO9947141 A1 | 9/1999 |
| WO | WO2005044214 A1 | 5/2005 |
| WO | WO2006040048 A1 | 4/2006 |
| WO | WO2011074143 A1 | 6/2011 |
| WO | WO2014132060 A1 | 9/2014 |

OTHER PUBLICATIONS

Stillman AE. Jaundice. In: Walker HK, Hall WD, Hurst JW, editors. Clinical Methods: The History, Physical, and Laboratory Examinations. 3rd edition. Boston: Butterworths; 1990. Chapter 87. Available from: https://www.ncbi.nlm.nih.gov/books/NBK413/.*
Wohlrab et al., Niacinamide—Mechanisms of Action and Its Topical Use in Dermatology, Skin Pharmacology and Physiology 2014;27:311-315.
Bissett et al., Topical niacinamide reduces yellowing, wrinkling, red blotchiness, and hyperpigmented spots in aging facial skin, International Journal of Cosmetic Science, 2004, vol. 26, pp. 231-238.
International Search Report and Written Opinion of the International Searching Authority, PCT/US2019/037430, dated Sep. 30, 2019, 12 pages.
www.gnpd.com Record ID: 2347755, Dark Circle Correcting Eye Swirl, Apr. 2014.

\* cited by examiner

*Primary Examiner* — Sahar Javanmard
(74) *Attorney, Agent, or Firm* — John G. Powell

(57) ABSTRACT

A method of degrading bilirubin in skin is provided. The method involves identifying a target portion of skin where a reduction in bilirubin level is desired, and applying a vitamin $B_3$-containing, low-pH composition to the target portion of skin during a treatment period. The composition contains an effective amount of a vitamin $B_3$ compound, has a pH of less than 5.0, and reduces bilirubin level in the target portion of skin during the treatment period. The amount of vitamin $B_3$ compound and the pH of the composition may be selected to provide a synergistic reduction in bilirubin level, as compared to the reduction in bilirubin level provided by the same composition at a neutral pH.

16 Claims, 2 Drawing Sheets

METHOD FOR DEGRADING BILIRUBIN IN SKIN

FIELD

The present disclosure is directed generally to a method of reducing the amount of bilirubin in skin. More specifically, the present disclosure is directed to a method that utilizes an effective amount of a vitamin $B_3$ compound in a low-pH composition to provide an improved bilirubin degradation benefit.

BACKGROUND

Bilirubin is a yellow pigment resulting from the catabolic breakdown of heme in red blood cells. As red blood cells age and breakdown, they are cleared from the body as part of the body's normal process of clearing waste products. Bilirubin is produced as part of this process. Typically, bilirubin is processed by the liver and then excreted from the body as waste. However, sometimes bilirubin can collect in skin tissue resulting in a yellow or sallow appearance. For example, bilirubin is responsible for the yellowish coloring associated with a bruise or jaundice. The yellow or sallow appearance caused by bilirubin in skin tissue is commonly associated with poor health (e.g., sickness, disease, malnutrition). Thus, it would be desirable to provide a way to improve the appearance of yellow or sallow looking skin resulting from bilirubin buildup.

One known method of reducing bilirubin levels in skin is through light therapy (a.k.a. photo therapy). Certain wavelengths of light react with bilirubin and convert it to a form that is more easily processed and removed by the body. Indeed, light therapy is one of the most common forms of reducing undesirably high bilirubin levels in newborn babies (i.e., hyperbilirubinemia). However, light therapy may require spending a significant amount of time (e.g., 12-72 hours) under an artificial light source, which is undesirable for many people suffering from such conditions. Accordingly, it would be desirable to provide a more convenient method of degrading bilirubin in skin to improve the appearance of a sallow-looking skin.

A limited number of cosmetic compositions are available that claim to improve the degradation of bilirubin. However, many, if not all, of these products are intended to be used to improve the appearance of undereye dark circles. For example, Eyedeline™ marine ingredient brand cosmetic eye care product from Lipotec purports to improve the appearance of undereye dark circles by enhancing bilirubin degradation, among other things. Truthinaging.com discloses that cosmetic and beauty products comprising N-hydroxysuccinimide, such as the eye serum product available from AQ Skin Solution, activate the elimination of blood originated pigments such as bilirubin, which contribute to the appearance of undereye dark circles. In another example, a botanical ingredient obtained from the White Bird of Paradise flower (commercially available as Vivillume™ from Lonza, N.J.) is claimed to degrade bilirubin. Cosmetic products sold by the Avani company (Spain) for treating undereye dark circles are advertised as including Vivillume™. Eye treatment products are formulated to treating the relatively small areas of skin present in the periorbital region of the face, and thus may not be suitable for treating larger areas of skin to address appearance issues associated with the presence of bilirubin in the skin (e.g., sallow-looking skin and/or uneven skin tone).

Accordingly, it would be desirable to provide an improved method of degrading bilirubin in skin. It would also be desirable to improve the appearance of sallow-looking skin and/or provide a more even skin tone, especially on the face and/or other areas of the body typically not covered by clothing.

SUMMARY

A method of degrading bilirubin in skin is described herein. The method comprises topically applying the vitamin $B_3$-containing compositions of the present invention to the skin of a person in need of treatment during a treatment period. The treatment period should of sufficient length for the composition to measurably degrade the amount of bilirubin present in the skin. The method can also improve the appearance of sallow-looking skin caused by bilirubin.

DETAILED DESCRIPTION

Figure 1:
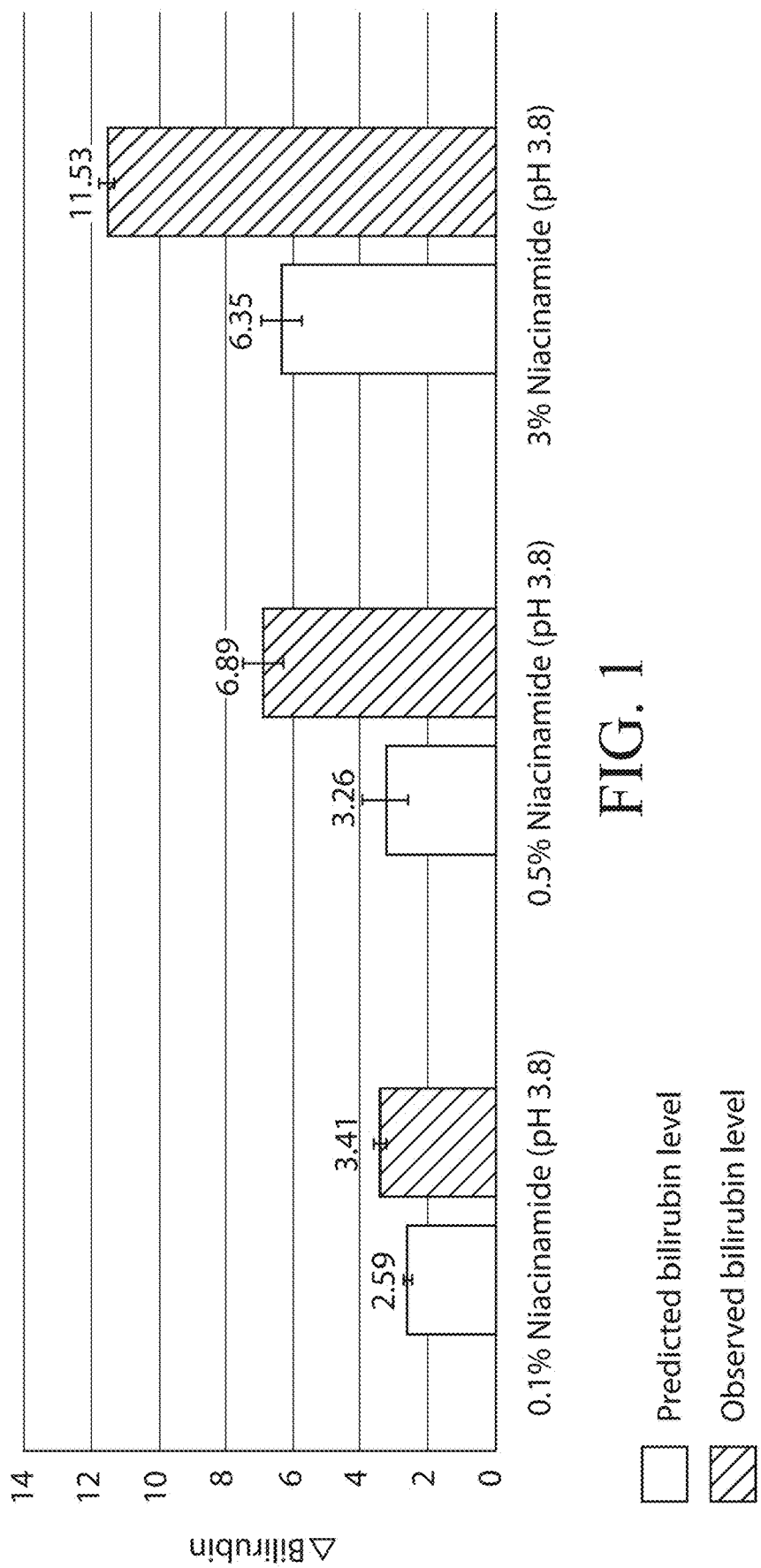
FIG. 1 is a bar chart comparatively illustrating the effect of niacinamide and pH on bilirubin reduction.

The drawbacks associated with the presence and/or buildup of bilirubin in skin are well known, but conventional treatments for reducing bilirubin levels in skin, such as light therapy, may not suitable for all users. Prior to the present discovery, it was unknown that a vitamin $B_3$ compound such niacinamide could reduce bilirubin level. It was also unknown that lowering pH of a treatment composition could reduce bilirubin levels. Surprisingly, it has also been discovered that the combination of niacinamide and low pH seems to provide a synergistic bilirubin degradation benefit.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"Apply" or "application", as used in reference to a composition, means to apply or spread the compositions of the present invention onto a human skin surface such as the epidermis.

"Bilirubin" means the compound identified as CAS No. 635-65-4 and having the chemical formula $C_{33}H_{36}N_4O_6$ and the following structure:

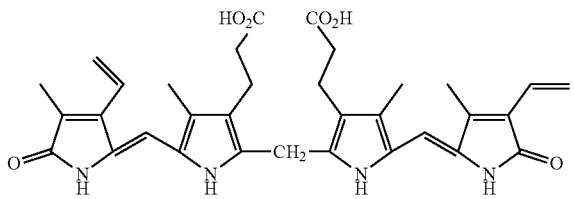 [SMILES: C=CC1=C(C)/C(=C/c2[nH]c(Cc3[nH]c(/C=C4\NC(=O)C(C)=C4C=C)c(C)c3CCC(=O)O)c(CCC(=O)O)c2C)NC1=O]

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of a vitamin $B_3$ compound is an amount sufficient to reduce the level of bilirubin in skin during a treatment period.

"Improve the appearance of" means providing a measurable, desirable change or benefit in male and/or female skin tone appearance, which may be quantified, for example, by a decrease in b* value of skin. Exemplary methods for determining improvements in appearance are described in more detail below.

"L*a*b*" refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e., negative a* values indicate green while positive a* values indicate magenta) and (iii) the position of the color between yellow and blue (i.e., negative b* values indicate blue and positive b* values indicate yellow).

"Low pH," as used herein, refers to cosmetic compositions that have a pH of between about 1.0 to about 5.0 (e.g., 1.5 to 5.0; 2.0 to 4.5, 2.5 to 4.0, or about 3.5). A suitable method of determining the pH of a composition is described in more detail below.

"Neutral pH" means a pH of between 5.0 and 8.0.

"Safe and effective amount" means an effective amount of an ingredient that is low enough to avoid serious side effects (within the scope of sound medical judgment).

"Sallow," when referring to the appearance of skin herein, means an unusual yellow or pale skin tone, with regard to a particular individual, which is commonly associated with an unhealthy state. Sallow-appearing skin can be diagnosed objectively (e.g., with a color value such as L* or b*) or subjectively (e.g., by a skin care professional or via self-diagnosis by a consumer).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Skin tone" means the overall appearance of basal skin color or color evenness. Skin tone is typically characterized over a larger area of the skin, which is generally more than 100 $mm^2$, up to and including the entirety of the facial skin or other bodily skin surface (e.g., arms, legs, back, hands, neck, chest and abdomen). Skin tone can be measured by image analysis. One measure of skin tone is lightness, which can be measured by the L* coordinate in the L*a*b* color space (International Commission on Illumination). Chromophore mapping such as melanin mapping and melanin concentration may also be used as an indicator of skin tone. Mean melanin may be calculated from the chromophore map data. Additionally, skin tone can be correlated to melanin evenness (e.g., standard deviation) which also may be calculated from the chromophore map data.

"Synergy" and variations thereof mean a bilirubin degrading effect provided by using niacinamide in combination with a low-pH composition that is more than the predicted additive effect of the vitamin $B_3$ compound and low pH.

"Treatment period," as used herein, means the length of time and/or frequency that a material or composition is applied to a target skin surface.

"Vehicle control" means a negative control that is identical to the test composition except that it does include the particular active(s) of interest (e.g., does not contain ribose).

Composition

The bilirubin degrading compositions herein are intended for topical application to human skin to provide a bilirubin degradation benefit. The compositions include an effective amount of a vitamin $B_3$ compound and have a pH of less than 5.0 (e.g., less than 4.5, 4.0, 3.5, 3.0, 2.5 or even about 2.0). The compositions are formed by mixing the vitamin $B_3$ compound with a dermatologically acceptable carrier. The compositions may optionally include one or more skin actives of the type commonly included in skin care compositions of the type. The compositions may be cosmetic compositions, pharmaceutical compositions, or cosmeceutical compositions, and may be provided in various product forms, including, but are not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition. The compositions herein may be made using conventional methods of making such compositions.

Vitamin $B_3$ Compound

The compositions of the present invention include a safe and effective amount of a vitamin $B_3$ compound. In addition to providing a bilirubin degradation benefit, the vitamin $B_3$ compound may also be useful for regulating other skin condition, for example, as described in U.S. Pat. No. 5,939,082. The compositions herein may contain 0.01% to 15%, by weight, of the vitamin $B_3$ compound, based on the weight or volume of the composition (e.g., 0.1% to 10%, 0.1% to 3%, 0.5% to 8%, 1% to 5%, or even 2% to 4%).

As used herein, "vitamin $B_3$ compound" means a compound having the formula:

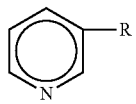

Where:
R is $CONH_2$ (i.e., niacinamide), COOH (i.e., nicotinic acid) or $CH_2OH$ (i.e., nicotinyl alcohol); derivatives thereof; and salts of any of the foregoing.

Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide.

Dermatologically Acceptable Carrier

The bilirubin degrading compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the vitamin $B_3$ compound can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 42.5 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Emulsifier the dermatologically acceptable carrier is in the form of an emulsion, it may be desirable to include an emulsifier to provide a stable composition (e.g., does not phase separate). When included, the emulsifier may be present at an amount of 0.1% to 10% (e.g., 1% to 5%, or 2%-4%). Emulsifiers may be nonionic, anionic or cationic. Some non-limiting examples of emulsifiers that may be suitable for use herein are disclosed in U.S. Pat. Nos. 3,755,560; 4,421,769; and McCutcheon's Detergents and Emulsifiers, North American Edition, pages 31.7-324 (1986).

Thickeners

In some instances, it may be desirable to use thickeners that tolerate a lower range of pH. For example, neutralized thickeners may degrade at lower pH and thus may not impart the desired thickening or feel properties to the composition. On the other hand, fatty alcohol thickeners such as cetyl alcohols and stearyl alcohols are generally stable at low pH (e.g., pH of less than 5.0 or even between a pH of about 2.5 to about 4.0), and thus may be particularly suited for use in the low pH compositions herein. Accordingly, the present compositions may be free or substantially free of neutralized thickeners and/or may have from 0.1% to 10% (e.g., from about 0.5% to about 8%, from about 1.0% to about 5%, or even from about 2% to about 4%) of a fatty alcohol thickener.

Other Optional Ingredients.

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Methods of Use

The present method includes identifying a target portion of skin on a person in need of treatment and applying a low-pH composition comprising a vitamin $B_3$ compound (e.g., niacinamide), and optionally one or more additional skin care agents, to the target portion of skin. The target portion of skin may be on a facial skin surface such as the forehead, perioral, chin, periorbital, nose, and/or cheek) or another part of the body (e.g., hands, arms, legs, back, chest). The person in need of treatment is one who exhibits an undesirable level of bilirubin in their skin. Bilirubin level may be determined according to any suitable method known in the art. For example, bilirubin level may be determined by a blood sample analysis. In another example, an undesirable bilirubin level may be indicated if the target portion of skin has a b* value greater than a predetermined threshold level corresponding to an undesirably high bilirubin level. The b* value may be determined according to the color imaging method described in more detail below. In some instances, a person may be identified as being in need of treatment when a target portion of skin has a yellow or sallow appearance and/or the person has an uneven skin tone. In another example, a person in need of treatment may be identified when an undesirable level of yellowness is determined to be present in a target portion of skin by an expert (e.g., dermatologist or cosmetologist). The person in need of treatment may also identify the target portion of skin, for example, when bruising is present. In some instances, a target portion of skin may not appear to be suffering from a buildup of bilirubin, but a user (e.g., a person suffering from or prone to jaundice or bruising) may still wish to treat the target portion of skin as a preventative measure (e.g., if the person is prone to conditions that cause bilirubin buildup such as jaundice).

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions improve the appearance of skin by reducing bilirubin level, as demonstrated by a reduction in b* of at least 5% (e.g., at least 10%, 15%, 20%, 25%, or more), according to the method hereinbelow. In some instances, a reduction in bilirubin level may be determined by measuring bilirubin levels according to a conventional in vivo method (e.g., blood analysis) and comparing the measured level to a predetermined threshold value or a level of bilirubin measured prior to the beginning of the treatment period.

The treatment period is ideally of sufficient time for the vitamin $B_3$ compound present in the low pH composition to reduce the bilirubin level of a target portion of skin. In some instances, the bilirubin reduction benefit provided by the low-pH composition may be demonstrated by a reduction in b* value relative to a predetermined b* value (i.e., a b* value determined prior to the beginning of the treatment period). Additionally or alternatively, the bilirubin reduction benefit may be demonstrated by comparing a b* value or measured bilirubin level to a control value (e.g., vehicle control) or a reference value (e.g., a similar composition with no niacinamide and/or having a neutral pH). The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented spot or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Bilirubin Degradation Assay

The bilirubin degradation assay provides an in vitro method of determining how a material or composition affects bilirubin degradation. Three replicates of each test sample are prepared in a 96-well plate (e.g., a FALCON brand 96-well tissue culture plate or equivalent) at a total volume of 250 µl/well. A stock of 250 ug/ml indirect bilirubin (i.e., the unconjugated form of bilirubin most commonly found in blood serum) is made by dissolving bilirubin powder (Cayman Chemicals Company, Catalog #17161) in DMSO (Sigma, Catalog # D8414-100 ml) to yield a stock solution at 10× working concentration. Working concentration of bilirubin is set at 25 ug/ml for every well except negative/vehicle control wells. The experimental set up typically includes positive control wells that contain 25 ug/ml bilirubin, 225 ul PBS, and 10% DMSO. The positive control wells may be prepared by mixing 25 ul of 250 ug/ml bilirubin stock solution and 225 ul PBS (AccuGENE, Catalog #51225). For negative/vehicle control wells, 25 ul DMSO is used in place of bilirubin. Test sample wells contain 25 ul of 250 ug/ml bilirubin stock solution, 200 ul PBS and 25 ul of each treatment solution made as 10× concentrate stock, e.g., for 0.1% Niacinamide treatment, a 10× concentrate stock is made at 1%.

The pH of each sample is adjusted using 1M HCl pH titration is performed separately before the experiment set up to determine how much 1M HCl is needed for each leg to achieve targeting pH level. 1500 ul of a master working solution of each testing leg was made without bilirubin to accommodate threshold volume need for pH adjustment. The master solution for the vehicle control wells contain 150 ul DMSO and 1350 ul of a mixture of 1M HCl and PBS. Bilirubin stock made in DMSO has similar pH to that of pure DMSO. Bilirubin is unstable when exposed to ambient light. Thus, for bilirubin positive control well pre-titration, DMSO was used as surrogate for bilirubin. The volume of 1M HCl needed for 1500 ul of bilirubin positive control master solution is similar to that of vehicle control master solution. For pre-titration test sample wells, 1500 ul of master solution is made by mixing 150 ul DMSO (surrogate for bilirubin stock), 150 ul 10× treatment stock, and a 1200 ul mixture of 1M HCl and PBS. For actual experimental set up, make: 1350 ul pre-mix in triplicate for each leg, less either DMSO (for vehicle control leg) or bilirubin (for positive control and treatment legs) but with matching volume of all other ingredients as determined by pre-titration. Then for vehicle control leg, add 25 ul DMSO per well followed by adding in 225 ul of the pre-mix. For all other legs, add 25 ul of 250 ug/ml bilirubin stock made in DMSO per well followed by adding in 225 ul of corresponding pre-mix. Such operation results in similar pH that has been pre-titrated using DMSO as surrogate for all bilirubin containing legs. The plate(s) containing the test samples are covered with aluminum foil and placed on top of a microplate shaker (VWR, Catalog #12620-938). Incubation was carried out at room temperature for 24-hr with constant shaking at 150 rpm. Bilirubin concentration was quantified after 24-hr incubation to determine the effect of bilirubin degradation as a result of active treatment in comparison to positive bilirubin control. Commercially available bilirubin quantification kit (Cell Biolab, Catalog # MET-5010) was used for bilirubin quantification. The assay is based on the Jendrassik-Grof method in which diazotized sulfanilic acid reacts with bilirubin to form azobilirubin, the latter of which can be detected at an OD of 540 nm. A standard bilirubin curve is generated using the same bilirubin used for treatment and quantified. Table 1 below provides a standard-curve setup.

TABLE 1

| Sample ID | Bilirubin concentration (µg/ml) | Making method |
| --- | --- | --- |
| Std1 | 200 | 300 ul of 500 ug/ml bilirubin stock in DMSO + 450 ul of PBS |
| Std2 | 100 | 300 ul of std1 + 300 ul of PBS |
| Std3 | 50 | 300 ul of std2 + 300 ul of PBS |
| Std4 | 25 | 300 ul of std3 + 300 ul of PBS |
| Std5 | 12.5 | 300 ul of std4 + 300 ul of PBS |
| Std6 | 5 | 300 ul of std5 + 450 ul of PBS |
| Std7 | 2.5 | 300 ul of std6 + 300 ul of PBS |
| Std8 | 0 | equal volume of PBS and DMSO |

Bilirubin concentrations of all testing legs are calculated using linear regression against the standard bilirubin curve. Resulting bilirubin concentrations are compared to neutral pH bilirubin reference leg. The difference in bilirubin quantification (Δ bilirubin) between the neutral-pH bilirubin reference leg and the low-pH niacinamide treated legs can be analyzed for predicted effect and actual effect.

Example

This example demonstrates the unexpected bilirubin degradation benefit of a low-pH composition comprising niacinamide by comparing the effects of niacinamide-containing compositions at neutral- and low-pH. The effect of niacinamide level on bilirubin degradation was tested at 0.1%, 0.5%, and 3%, by weight, based on the volume of the composition (w/v). A vehicle control is used in this Example as the negative control. The bilirubin levels in this Example were determined according to the method above. The average bilirubin level of the composition in the pH 7.4, 0% niacinamide test leg was used as a reference value to calculate changes in bilirubin level for the other test legs. "IB" in Table 2 refers to indirect bilirubin, which is known to those skilled in the art. The bilirubin values provided in Table 2 are averages of the triplicate samples of the corresponding test leg. The actual change in bilirubin level for each test leg is determined by subtracting the average bilirubin level from the reference value. The predicted change in bilirubin level is determined by adding 2.323 to the bilirubin level measured at pH 7.4 for the 0.1%, 0.5%, and 3% (w/v) niacinamide test legs. The 2.323 value corresponds to the observed pH effect, which is the change in bilirubin level associated with the difference in pH for the 0% niacinamide solution. The results of the test are summarized in Table 2 below and illustrated in FIG. 1.

TABLE 2

| Sample (25 µg/mL IB) | Avg. IB at pH 7.4 (µg/mL) | Avg. IB at pH 3.8 (µg/mL) | Δ IB (actual) | Δ IB (predicted) | p-value |
|---|---|---|---|---|---|
| Vehicle | 1.979 | 1.667 | N/A | N/A | N/A |
| 0% niacinamide | 21.118 | 18.795 | 2.323 | N/A | 1.000 |
| 0.1% (w/v) niacinamide | 20.851 | 17.713 | 3.405 | 2.590 | 0.004 |
| 0.5% (w/v) niacinamide | 20.185 | 14.231 | 6.887 | 3.256 | 0.002 |
| 3% (w/v) niacinamide | 17.087 | 9.585 | 11.533 | 6.354 | 0.000 |

As illustrated in Table 2 and FIG. 1, increasing the niacinamide level and lowering the pH of the solution both improve the ability of the composition to decrease bilirubin levels. However, when niacinamide is included in the low-pH composition, the reduction in bilirubin occurs at a much higher level than predicted based on the observed individual effects of pH and niacinamide level. Thus, providing a low-pH skin care composition that includes a vitamin $B_3$ compound may provide a better way to improve the appearance of sallow-looking skin caused by bilirubin buildup in skin tissue.

Correlating Bilirubin Concentration to Yellowness.

To detect yellowness (b*), a suitable spectrophotometer is set to collect absorbance spectrum from 350 nm to 750 nm in 10 nm increments. The absorbance spectrum from the yellowness measurement are then converted to L*a*b* values by a computer using suitable conversion software.

It is believed, without being limited by theory, that bilirubin concentration in skin has a direct correlation to a yellow or sallow appearance. To determine the correlation between bilirubin concentration and yellowness, a bilirubin standard curve was set up. Bilirubin powder (Cayman Chemicals Company, Catalog #17161) was dissolved in DMSO (Sigma, Catalog # D8414-100 ml) to make 500 ug/ml bilirubin stock. This concentrate bilirubin stock was diluted in PBS as shown in Table 1 above to yield bilirubin levels at 50, 25, 12.5, 5, 2.5, and 0 ug/ml. The samples were loaded into a 96-well plate in triplicate and the absorbance was measured using the spectrophotometer at 350 nm to 750 nm in 10 nm increments. The results of this test are illustrated in Table 3 and FIG. 2.

TABLE 3

| Bilirubin Concentration (µg/mL) | Average b* value |
|---|---|
| 0 | −0.417 |
| 2.5 | 4.258 |
| 5 | 8.582 |
| 12.5 | 23.889 |
| 25 | 47.993 |
| 50 | 90.017 |

Figure 2:
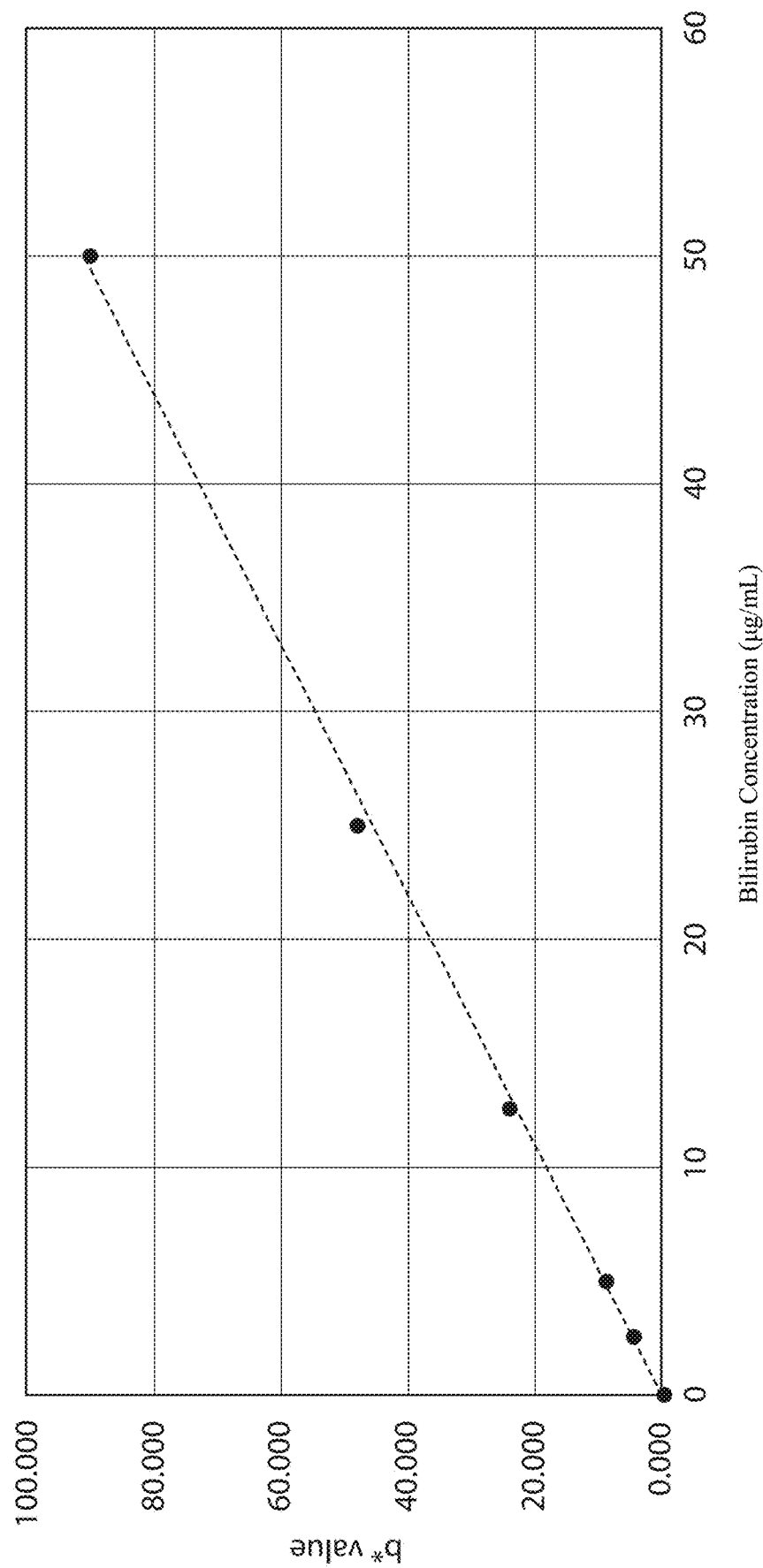
FIG. 2 is line chart illustrating the direct correlation between bilirubin level and b* value.

As shown in Table 3 and FIG. 2, the b* scores as converted by suitable computer software show linear correlation to bilirubin concentration in the range from 0 ug/ml to 50 ug/ml bilirubin. Human biological bilirubin concentration falls within this concentration range.

Examples/Combinations

A. A method of degrading bilirubin in skin, comprising:
   a) identifying a target portion of skin on a person in need of treatment; and
   b) applying a low-pH composition to the target portion of skin during a treatment period, wherein the low-pH composition comprises an effective amount of a vitamin $B_3$ compound, has a pH of less than 5.0, and reduces bilirubin level in the target portion of skin during the treatment period.
B. The method of paragraph A, wherein the pH of the composition is 4.0 or less, preferably between 2.0 and 4.0.
C. The method of paragraph A or B, wherein the composition comprises about 0.01% to about 10%, preferably 0.1% to 5%, of the vitamin $B_3$ compound.
D. The method of any preceding paragraph, wherein the composition reduces bilirubin level by at least 10% during the treatment period.
E. The method of any preceding paragraph, wherein the effective amount of niacinamide and the pH of the composition are selected to provide a synergistic reduction in bilirubin level relative to the same composition at a neutral pH.
F. The method of paragraph E, wherein the synergistic reduction in bilirubin level is at least 10% more than a predicted additive amount of bilirubin reduction.
G. The method of any preceding paragraph, further comprising at least one additional skin care active selected from the group consisting of vitamins, minerals, peptides, sugar amines, sunscreens, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, and combinations thereof.
H. The method of any preceding paragraph, wherein the vitamin $B_3$ compound is selected from niacinamide, nicotinic acid, nicotinyl alcohol, derivatives of these, and combinations thereof.
I. The method of the paragraph H, wherein the vitamin $B_3$ compound is niacinamide
J. The method of any preceding paragraph, further comprising about 0.1% to about 10% of a stable fatty alcohol thickener.
K. The method of paragraph J, wherein the composition provides a reduction in b* value of at least 5% relative to a b* value that is determined prior to the treatment period.
L. The method of any preceding paragraph, wherein the target portion of skin in need of treatment exhibits a sign of jaundice or bruising.
M. The method of any preceding paragraph, wherein the low-pH composition is only applied to the target portion of skin when bilirubin level exceeds a predetermined threshold value.
N. The method of paragraph M, wherein the composition provides a reduction in b* value of at least 5% relative to a predetermined b* value.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of degrading bilirubin in skin, comprising:
   a) identifying a target portion of skin on a person in need of treatment; and
   b) applying a low-pH composition to the target portion of skin during a treatment period, wherein the low-pH composition comprises an effective amount of niacinamide, has a pH between 2 and 5, and reduces bilirubin level in the target portion of skin during the treatment period.

2. The method of claim 1, wherein the pH of the composition is 4.0 or less and the composition comprises about 0.01% to about 10% of niacinamide.

3. The method of claim 1, wherein the composition reduces bilirubin level by at least 10% during the treatment period.

4. The method of claim 1, wherein the effective amount of niacinamide and the pH of the composition are selected to provide a synergistic reduction in bilirubin level relative to the same composition at a neutral pH.

5. The method of claim 4, wherein the synergistic reduction in bilirubin level is at least 10% more than a predicted additive amount of bilirubin reduction.

6. The method of claim 1, further comprising at least one additional skin care active selected from the group consisting of vitamins, minerals, peptides, sugar amines, sunscreens, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, and combinations thereof.

7. The method of claim 1, further comprising about 0.1% to about 10% of a stable fatty alcohol thickener.

8. The method of claim 1, wherein the target portion of skin in need of treatment exhibits a sign of jaundice or bruising.

9. A method of improving the appearance of sallow-looking skin, comprising:
   a. determining a bilirubin level for a target portion of skin; and
   b. applying a skin care composition to the target portion of skin during a treatment period when the bilirubin level exceeds a predetermined threshold value, wherein the skin composition comprises an effective amount of niacinamide, has a pH between 2 and 5, and reduces bilirubin level in the target portion of skin during the treatment period.

10. The method of claim 9, wherein the composition provides a reduction in b* value of at least 5% relative to a predetermined b* value.

11. The method of claim 9, wherein the cosmetic composition includes about 0.01% to about 15% niacinamide.

12. The method of claim 9, wherein the pH is between about 2.5 and 5.0.

13. The method of claim 9, further comprising about 0.1% to about 10% of a stable fatty alcohol thickener.

14. The method of claim 9, further comprising at least one additional skin care active.

15. The method of claim 9, wherein the composition reduces the bilirubin level below the threshold level.

16. The method of claim 9, wherein the composition reduces the bilirubin level by at least 10%.

* * * * *